United States Patent [19]

Copelin

[11] 4,294,998
[45] Oct. 13, 1981

[54] PREPARATION OF HIGH PURITY 1,4-BUTANEDIOL

[75] Inventor: Harry B. Copelin, Wilmington, Del.

[73] Assignee: E. I. Du Pont de Nemours and Company, Wilmington, Del.

[21] Appl. No.: 174,258

[22] Filed: Jul. 31, 1980

Related U.S. Application Data

[63] Continuation-in-part of Ser. No. 920,123, Jun. 28, 1978.

[51] Int. Cl.$^3$ .............................................. C07C 29/78
[52] U.S. Cl. .................................................. 568/868
[58] Field of Search ................................ 568/868, 854

[56] References Cited

U.S. PATENT DOCUMENTS

| | | | |
|---|---|---|---|
| 2,686,817 | 8/1954 | Copes et al. | 568/867 |
| 3,467,679 | 9/1969 | Rogers | 260/346.1 |
| 3,852,164 | 12/1974 | Chow et al. | 203/91 |
| 4,081,257 | 3/1978 | Lassmann et al. | 568/868 |

FOREIGN PATENT DOCUMENTS 959366  9/1956  Fed. Rep. of Germany.
2060548  6/1972  Fed. Rep. of Germany ...... 568/868

OTHER PUBLICATIONS

Kirk–Othmer "Encyclopedia of Chemical Technology" Interscience, Publ. 2nd Ed., vol. 10, pp. 249; 668 (1967).
Weissberger, Arnold, Ed. "Techniques of Organic Chemistry" vol. III, Part I, "Separation and Purification", Interscience, Publ. (1956) pp. 396–397, 528–529, 542–543, 548–549 & 555–558.
CRC Handbook of Chemistry and Physics, 60th Edition (1979–1980) pp. C-220 and C-312.

*Primary Examiner*—Natalie Trousof
*Assistant Examiner*—L. Hendriksen

[57] ABSTRACT

A process for the purification of crude 1,4-butanediol by crystallizing said crude in a solution comprising tetrahydrofuran at a temperature of from 10° to −10° C. and a pressure of from 16–26 mm of mercury to form a slurry of crystallized 1,4-butanediol in a liquid, and then separating the crystallized 1,4-butanediol from the liquid.

13 Claims, 1 Drawing Figure

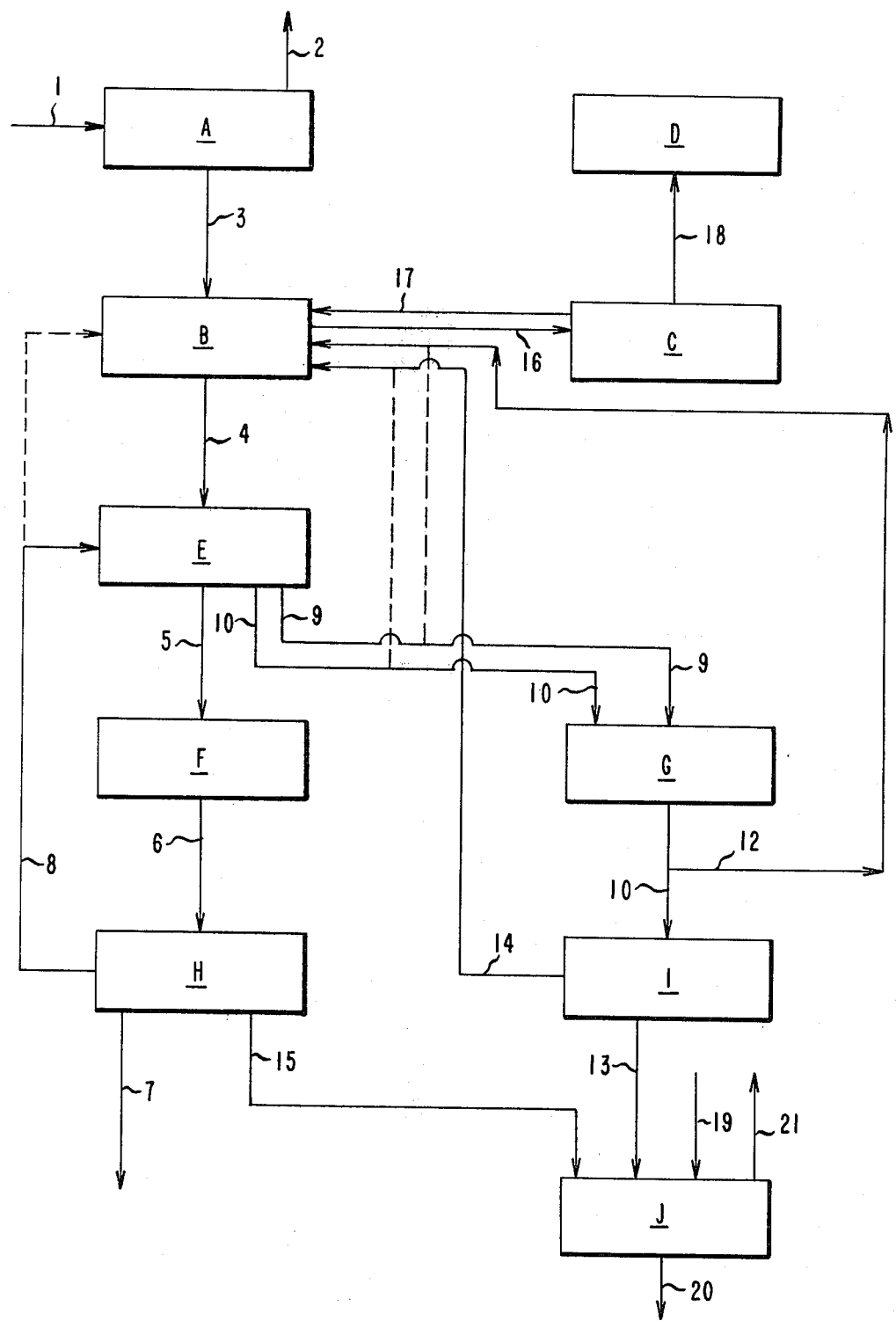

PREPARATION OF HIGH PURITY 1,4-BUTANEDIOL

CROSS-REFERENCE TO RELATED APPLICATION

This application is a continuation-in-part of application Ser. No. 920,123, filed June 28, 1978.

DESCRIPTION

1. Technical Field

This invention relates to a process for preparing high purity 1,4-butanediol, said process comprising crystallizing crude 1,4-butanediol from solution in tetrahydrofuran. This invention also relates to a process for preparing high purity 1,4-butanediol by crystallizing crude 1,4-butanediol in a tetrahydrofuran solution and after recovering crystallized 1,4-butanediol, converting the 1,4-butanediol remaining dissolved in the tetrahydrofuran solution to tetrahydrofuran.

2. Background Art

U.S. Pat. No. 3,852,164 discloses the purification of 1,4-butanediol by vacuum distillation. However, in order to attain higher purities, successive fractionations are necessary. At the present time, it is believed that all of the commercial processes for the purification of 1,4-butanediol involve one or more fractionations by processes similar to that of the aforesaid patent.

Other methods for refining 1,4-butanediol are disclosed, for example, German Pat. No. 959,366 which discloses the crystallization by cooling of 1,4-butanediol from a suspension of 1,4-butanediol and a liquid in which the 1,4-butanediol is insoluble to produce exceptionally pure 1,4-butanediol. However, the removal of all of the insoluble liquid from the crystals cannot be readily achieved; and there is, therefore, a new impurity introduced into the 1,4-butanediol.

U.S. Pat. No. 2,789,147 discloses the purification of 2-butyne-1,4-diol by subjecting impure 2-butyne-1,4-diol, having a solidification point of 49°–52° C. and a water content ranging from 1–4%, to a sweating operation wherein the temperature is lowered from the solidification point to the eutectic point and the liquid phase is separated from the crystals that are formed. Such a process, however, involves a very inefficient method of heat removal.

Thus, it is known to purify 2-butyne-1,4-diol by solidification by cooling. It is also known to purify 1,4-butanediol by solidification in an insoluble liquid. However, the solidification by cooling of 1,4-butanediol in tetrahydrofuran is not disclosed.

DISCLOSURE OF THE INVENTION

Now it has been found that high purity 1,4-butanediol can be prepared by a process comprising (a) crystallizing 1,4-butanediol from a crystallizer solution consisting essentially of tetrahydrofuran, 1,4-butanediol and impurities at a temperature that is maintained by evaporative cooling at from 10° to −10° C. to form a slurry of crystals of 1,4-butanediol and liquid; and (b) separating the crystals of 1,4-butanediol and the liquid.

The present process is unique in its use of tetrahydrofuran as a solvent for the crystallization of 1,4-butanediol and surprisingly results in the preparation of 1,4-butanediol with a purity higher than heretofore possible by distillation. The present process also results in a substantial reduction in energy required relative to processes involving distillation. Approximately 30% less energy is required in the present process relative to a two-column distillation.

The crystallizer slurry of crystals and liquid in the crystallizer should generally be maintained at from 10–20% solids of 1,4-butanediol crystals, preferably from 14–16% solids. Solids levels below 10% require substantially more centrifuge capacity. Solids levels above 20% result in a slurry of too great a viscosity for efficient handling. The percent solids in the slurry affects the centrifuge capacity and pumpability of the slurry. The percent solids of crystals in the crystallizer are controlled by the temperature of crystallization and the composition of the crystallizer mixture. Changes in the composition of the crystallizer solution changes its freezing point. As the temperature is reduced more crystals are produced. At temperatures below −10° C., the percent solids will reach greater than 20% at the crystallizer solution compositions of this invention.

The use of tetrahydrofuran in the crystallizer is particularly advantageous over other liquids because tetrahydrofuran is a natural decomposition product of 1,4-butanediol. The use of other liquids for said crystallization would add at least one additional impurity in the refined 1,4-butanediol that would not be present when tetrahydrofuran is used. Additionally, the use of other liquids in many instances raises a problem with respect to the separation of that liquid from the tetrahydrofuran and from the refined 1,4-butanediol. Tetrahydrofuran can be separated from the 1,4-butanediol rather easily. However, tetrahydrofuran is not so easily separated from e.g., liquids such as methanol, isopropanol and other liquids in which 1,4-butanediol is soluble. Tetrahydrofuran is also advantageous in the present invention because its actually measured vapor pressure in the crystallizer solution is greater than its theoretical vapor pressure thereby permitting evaporative cooling of the crystallizer solution at higher operating pressures. Additionally, tetrahydrofuran permits crystallization of 1,4-butanediol at higher pressures than when solvents like isopropanol, methanol or ethanol are used at the same operating temperature.

Cooling of the crystallizer solution of the present invention is directed to evaporative cooling. Under evaporative cooling, the presence of tetrahydrofuran permits the crystallization at practical pressure and temperatures. The temperature for the crystallization is generally from 10° to −10° C., preferably from −4° to −8° C., and most preferably −5° to −7° C. This temperature range is preferably achieved by evaporative cooling by vaporization of the tetrahydrofuran at the preferred pressure of from 16–26 mm mercury absolute, most preferably 18–22 mm Hg absolute. At other pressures the present process is operable, but the advantages are not as great. The viscosity of crystallizer solution at a temperature in the range of 10° to −10° C. will be under 1000 centipose and therefore poses no handling problem as long as the amount of tetrahydrofuran in the crystallizer solution is maintained in the range indicated herein.

The crystals that result are very high purity 1,4-butanediol. The crystals can be melted and then distilled to remove tetrahydrofuran and water and give a purified 1,4-butanediol. The thus purified 1,4-butanediol possesses advantages of purity and color over 1,4-butanediol that is merely purified by distillation without crystallization. It is, however, possible to further purify said crystals by first removing liquid adhering to the crystal surface. This liquid on the 1,4-butanediol crystal surface can be removed by washing with a wash solution. The liquid from the slurry separated in Step (b) above and the liquid from the crystal surface is referred to herein as mother liquor.

There is only one wash solution, aside from 1,4-butanediol itself, that will remove the mother liquor with all its impurities from the crystal surface and not merely replace said impurities with different impurities without excessive dissolving of crystals of pure 1,4-butanediol. The preferred wash solution of the present invention is such a solution and comprises tetrahydrofuran and water with or without 1,4-butanediol. The amount of water may vary from trace quantities to substantially larger amounts, e.g., 5–10% by weight. A wash solution composed of, for example, methanol, isopropanol or other liquid solvents, would remove the mother liquor from the crystal surface and leave itself there in place of the mother liquor. In such a case, it would still be necessary to remove the solvent from the 1,4-butanediol liquid that results after the crystals are melted. It is possible to remove such solvents from 1,4-butanediol but their presence is undesirable since they (1) must be removed and (2) introduce new impurities into the system wherein the 1,4-butanediol is recovered that were not present before. The amount of tetrahydrofuran in the wash solution may vary. The wash solution can be essentially all tetrahydrofuran or tetrahydrofuran and water or tetrahydrofuran, 1,4-butanediol and water. Although the wash solution may be essentially all tetrahydrofuran, it is preferably a mixture of tetrahydrofuran, 1,4-butanediol and water such that excessive amounts of crystals of 1,4-butanediol will not be dissolved. It is most preferred, however, to use a stream from the distillation of the melted crystals of 1,4-butanediol that contain tetrahydrofuran, water and 1,4-butanediol as a wash solution. The crystals of 1,4-butanediol can be washed in the separator, e.g., the centrifuge, or they can be washed in another facility as a separate operation.

The use of the wash solution of this invention removes mother liquor from the crystals surface and replaces the mother liquor with compounds that are already present in the system and that are substantially all tetrahydrofuran and compounds convertible to tetrahydrofuran. Additionally, the wash solution removes impurities from the crystal surface. The tetrahydrofuran and water that is left on the crystal surface can be removed from the 1,4-butanediol by distillation. Since tetrahydrofuran is a decomposition product of 1,4-butanediol that is formed when 1,4-butanediol is processed, the distillation step adds nothing to the steps required for purification. That is, the tetrahydrofuran from the wash liquor is merely removed when the tetrahydrofuran that normally forms as a decomposition product, is removed. Removal of the tetrahydrofuran from the 1,4-butanediol can be achieved by distillation or refining procedures well known in the art.

Accordingly, the crystals of 1,4-butanediol are separated from the mother liquor, washed with a wash solution comprising tetrahydrofuran and water with or without 1,4-butanediol, and then separated from the wash liquor. The resultant 1,4-butanediol crystals are very high purity. However, even higher purity 1,4-butanediol can be obtained, if the crystals after washing are melted and subjected to a single distillation to remove impurities. The wash liquor can be recycled to the crystallizer or added to the mother liquor.

Another embodiment of the process of the present invention comprises converting to tetrahydrofuran the 1,4-butanediol as well as any other compounds that are convertible to tetrahydrofuran that are present in the mother liquor and/or the wash liquor by (c) washing the crystals of 1,4-butanediol after the mother liquor is separated therefrom with a wash solution comprising tetrahydrofuran, water with or without 1,4-butanediol and separating the washed crystals and liquor;

(d) melting the washed crystals to form liquid 1,4-butanediol and distilling the 1,4-butanediol to give a distillate of tetrahydrofuran, water with or without 1,4-butanediol, a residue and purified 1,4-butanediol;

(e) distilling any portion of the mother liquor and/or wash liquor after 1,4-butanediol crystals are separated therefrom, to yield a distillate of tetrahydrofuran and water and a residue;

(f) recovering the distillate from (d) and (e);

(g) converting the residue from (d) and (e) to a reaction product comprising tetrahydrofuran by acid cyclization at from 100°–150° C.; and (h) separating the tetrahydrofuran from the reaction product from the cyclization.

The distillate from (d) and (e) can be recycled to the crystallizer, used as a wash solution or sent to tetrahydrofuran refining facilities for recovering tetrahydrofuran. Part of the tetrahydrofuran prepared from the residue in (d) and (e) can be recycled as make up to the crystallizer or can be sent to tetrahydrofuran refining facilities for recovering tetrahydrofuran. A portion or all of the mother liquor and/or wash liquor may be sent directly to cyclization for conversion to tetrahydrofuran by passing step (e) above.

Crystallization of crude 1,4-butanediol in tetrahydrofuran coupled with further treatment by way of recovery of valuable materials present in the mother liquor is especially advantageous where there are present tetrahydrofuran preparation facilities. The process of the present invention advantageously makes it possible to achieve a highly purified 1,4-butanediol coupled with the recovery of 1,4-butanediol and other compounds convertible to tetrahydrofuran. The disposal problem that exists, where a material other than tetrahydrofuran is used, raises a difficult problem. These problems relate not only to disposal but also to losses that make mere crystallization less attractive economically. Tetrahydrofuran is the decomposition product that is formed when 1,4-butanediol is processed. The recovery of this tetrahydrofuran and the tetrahydrofuran that is prepared from materials convertible to tetrahydrofuran makes this embodiment especially advantageous.

The crude 1,4-butanediol that is fed to the crystallizer contains 1,4-butanediol and impurities. Since the purification process of the invention is a purely physical one, it will remove impurities, regardless of their chemical natures, so long as they are soluble in tetrahydrofuran at the operating temperatures of the process, i.e., $-10°$ to $+10°$ C. Any impurity will be removed from 1,4-butanediol to the extent of its solubility in tetrahydrofuran. This being so, the process by which the crude 1,4-butanediol starting material is prepared and the consequent chemical nature of its impurities are irrelevant. However, since large amounts of 1,4-butanediol are presently made by catalytically reacting acetylene and formaldehyde to form 1,4-butynediol and then hydrogenating the butynediol to 1,4-butanediol, crude 1,4-butanediol made by that process is preferred as a starting material, but only because of its availability. Crude 1,4-butanediol made by other methods, e.g., by the reaction of propylene and acrolein, or from furan, can also be used as a starting material.

The amount of 1,4-butanediol in the crude 1,4-butanediol can vary broadly. The process of the present invention is equally applicable, for example, to crude 1,4-butanediol of 50% purity or 97% purity.

The water content of the crude 1,4-butanediol fed to the crystallizer of the process of the present invention can vary rather broadly. This water content may be very low or it may be as high as 18% by weight. Generally, crude 1,4-butanediol containing less than 10%, by weight, of water can be fed to the crystallizer. However, to obtain operating advantages, the amount of water introduced into the crystallizer solution by the crude 1,4-butanediol should not exceed 13%, preferably 6.5%, by weight of the solution.

The water content of the crude 1,4-butanediol, if necessary, is adjusted generally by flash evaporation, although other conventional means of removing water may be used before the crude is subjected to the present process.

The crystallizer solution comprises the liquid composition and crude 1,4-butanediol. The liquid composition is made up of tetrahydrofuran, 1,4-butanediol and impurities such as water, miscellaneous salts and high and low boilers. The liquid composition of this invention can be made up of one or more of three flows. Mother liquor, wash liquor and tetrahydrofuran/water distillate that is removed from mother liquor and/or wash liquor can be used to make up what is referred to as the liquid composition. The amount of tetrahydrofuran present in the liquid composition can vary rather broadly in the process of the present invention. However, generally because of operating advantages, the amount of tetrahydrofuran should be maintained at whatever is necessary to maintain 14-50% by weight tetrahydrofuran in the crystallizer solution, preferably 20-30% by weight and most preferably 20-25%. The tetrahydrofuran, because of its relatively high vapor pressure, cools the liquid composition by evaporation to maintain the crystallization temperatures of the present process. The tetrahydrofuran also reduces the viscosity of the liquid composition thereby increasing the capacity of the centrifuges used to separate crystals at any given solids level. The amount of heat removed determines the percentage of crystallization of the crude 1,4-butanediol. The amount of tetrahydrofuran in the liquid composition as well as the water, 1,4-butanediol and impurities affects the freezing point of the liquid composition. Any increase in the percent of tetrahydrofuran in the liquid composition (1) lowers the crystallization temperature at a given pressure, (2) reduces the viscosity of the liquid composition and (3) increases the absolute pressure needed to vaporize the tetrahydrofuran at any given temperature. There is, of course, present in the liquid composition 1,4-butanediol that was dissolved in the tetrahydrofuran under the process conditions. The amount of 1,4-butanediol in the liquid composition can vary broadly. However, it generally is made up of sufficient 1,4-butanediol to attain a concentration of 35-84% by weight, preferably 61-74%, most preferably 67-73.5% in the crystallizer solution. The balance of the crystallizer solution is of impurities defined as water, miscellaneous salts and high and low boilers amounting generally to 2-15% by weight, preferably 6-9%, most preferably 6.5-8%.

What is meant by miscellaneous salts is sodium, aluminum and nickel salts that are usually present in 1,4-butanediol synthesis. What is meant by high and low boilers are materials that boil above or below 1,4-butanediol and may include materials convertible to tetrahydrofuran.

The water content of the liquid composition, like the tetrahydrofuran content, affects the process. Since the water affects the vapor pressure of the liquid composition and the crystallization temperature, its presence must be closely regulated. Generally, the water content of the liquid composition may be at whatever level will give a water content of 0-13% by weight in the crystallizer solution, preferably 5-7% by weight. For each 1% rise in water content in the crystallizer solution, the freezing point of the solution decreases about 1.8° C.

Mother liquor separated from the slurry of crystals of 1,4-butanediol from the crystallizer can be recycled to the crystallizer directly or it can be combined with wash liquor and recycled to the crystallizer. The mother liquor may, before any distillation to remove tetrahydrofuran, be sent directly to cyclization for conversion to tetrahydrofuran. The mother liquor alone or the combination of mother liquor and wash liquor with the distillate containing tetrahydrofuran and water from the distillation of mother liquor and/or wash liquor can be adjusted to give the desired composition in the crystallizer solution.

Wash solution can be produced by the distillation of melted crystals of 1,4-butanediol from crystallization after washing. The distillate from this distillation is usually composed of tetrahydrofuran, 1,4-butanediol and water. The wash solution does not require 1,4-butanediol and water, but it is convenient that it contain 1,4-butanediol and water because of the availability of the aforesaid distillate. The wash solution can be tetrahydrofuran and water.

The removal of impurities such as miscellaneous salts, water, high and low boilers from the crystallizer system can be accomplished by removing a portion of the wash liquor and/or mother liquor stream after first distilling the stream to recover tetrahydrofuran. This recovered tetrahydrofuran, along with water that is vaporized with it, can be recycled back to the crystallizer or, if not needed to maintain the tetrahydrofuran level in the crystallizer solution, the recovered tetrahydrofuran-water mixture can be sent to tetrahydrofuran purification facilities. The residue from the distillation of wash liquor and/or mother liquor is cyclized in the presence of an acid catalyst to form tetrahydrofuran.

The residue from the distillation of the melted crystals of 1,4-butanediol can also be cyclized therewith to form tetrahydrofuran. The material from cyclization after tetrahydrofuran removal can be disposed of. The tetrahydrofuran can be sent to refining and recovery facilities for tetrahydrofuran.

In a preferred embodiment of the present process, the use of a centrifuge to separate the crystallized 1,4-butanediol and mother liquor permits the attaining of a highly purified 1,4-butanediol in a single crystallization step. Where the separation is by filtration, the purity of the 1,4-butanediol may be lower than the purity of 1,4-butanediol that is obtained when the separation is by centrifuge unless considerably more wash solution or more than one crystallization is used. Thus, the purity that is normally achieved by multiple crystallizations can be achieved by one crystallization when a centrifuge is used to separate the crystallized 1,4-butanediol. However, in order to maximize the purity of the 1,4-butanediol, a perforated bowl centrifuge is preferred in view of the lower purities obtained when the bowl is not perforated. An example of a perforated bowl centrifuge is a Model CH centrifuge manufactured by International Equipment Co. The Model CH centrifuge has a perforated bowl fitted with a 100 mesh stainless steel screen. One crystallization with the use of the aforesaid perforated bowl centrifuge was sufficient to increase the purity of the 1,4-butanediol to greater than 99%.

The process of the present invention includes a further embodiment involving the conversion of the dissolved 1,4-butanediol and other convertible compounds in the various liquid streams to tetrahydrofuran.

The FIGURE provided is a flow chart attempting to illustrate some of the embodiments of this invention.

Referring now to the FIGURE, crude 1,4-butanediol 1 is fed to a flash evaporator A wherein the water content is reduced. Water 2 exits the evaporator A. The crude 1,4-butanediol with reduced water content 3 is fed to a crystallizer B containing a liquid composition to form a crystallizer solution. The crystallizer pressure is such that tetrahydrofuran vapors 16 flow from the crystallizer to a condenser C and condensed tetrahydrofuran 17 flows from the condenser C back to the crystallizer B. Noncondensable vapors 18 flow from the condenser C to vacuum pump D. Crystallized 1,4-butanediol 4 in a slurry with liquid enters a centrifuge E. Mother liquor 9 exits the centrifuge E and can be collected in the mother liquor/wash liquid tank G and/or recycled to the crystallizer. Wet 1,4-butanediol cake 5 exits the centrifuge E and enters melt tank F. Melted 1,4-butanediol 6 flows from the melt tank F to a distillation column H. Refined 1,4-butanediol 7 leaves the refiner H to storage. Bottoms from the distillation column H can be sent to a cyclization reactor J. Tetrahydrofuran and water with or without 1,4-butanediol 8 leave the distillation column H and can be sent to the centrifuge E as wash solution and/or recycled to the crystallizer. Wash liquor 10 from the centrifuge E can be sent to the mother liquor/wash liquor tank G and/or recycled to the crystallizer. The entire flow of mother liquor and/or wash liquor can be sent to cyclization or portions of the mother liquor and/or wash liquor 11 can flow to a mother liquor still I. The remaining mother liquor/wash liquor 12 from the mother liquor/wash liquor tank can be recycled to the crystallizer B. Tetrahydrofuran and water 14 from the mother liquor still I can be sent to the crystallizer B. The mother liquor still I can be operated so that the water in the tetrahydrofuran-water stream is the equivalent to the water content of the crude 1,4-butanediol entering the crystallizer. The residue 13 from the mother liquor still I which contains essentially all the impurities in the incoming crude 1,4-butanediol enters the cyclization reactor J where materials in the mother liquor are converted to tetrahydrofuran in the presence of acid catalyst 19. Tetrahydrofuran 21 from the cyclization reactor J can be sent to tetrahydrofuran refining and recovering facilities. Residue 20 exits the cyclization reactor J and can be sent to disposal systems.

The following percentage of impurities, other than THF, in the crystallized 1,4-butanediol were achieved by the process of the present invention with the separation indicated:

|  | % Impurities THF/H$_2$O Free Basis |
| --- | --- |
| Slurry exit of crystallizer | 0.833 |
| Unwashed crystals out of solid bowl centrifuge | 0.544 |
| Unwashed crystals out of perforated basket centrifuge | 0.083 |
| Washed crystals out of perforated basket centrifuge | 0.060 |

The above impurities were determined by using a Perkin-Elmer 910 chromatograph.

Thus, it can be seen that the impurities that are present in the 1,4-butanediol after the present process are dramatically reduced. Purities as high as 99.98% are possible by the process of this invention. The purification by distillation of crude 1,4-butanediol is known in the art. For example, U.S. Pat. No. b 3,891,511 discloses a method for the distillation of crude 1,4-butanediol where 1,4-butanediol is obtained with a purity varying from 98.3% to less than 99.7%. Generally, purities greater than 99.5% cannot be attained by distillation.

Relatively large decreases in impurity content by the present process as compared to distillation processes are achieved. The improvement in purity resulting from the decrease in impurities results in reduced color which permits the use of the 1,4-butanediol in the preparation of a color-free polyester. In order to achieve the purity attained by this process successive distillations are required.

BEST MODE

Crude 1,4-butanediol is fed to a flash evaporator operated at 100 mm Hg pressure to reduce the water content to a range of 3-4%, by weight. The residue or bottoms from the flash evaporator (crude 1,4-butanediol) is cooled to about 30° C. and then introduced into liquid composition at from −4° to −8° C. at a pressure of 16-26 mm Hg absolute in a crystallizer vessel. The crystallizer solution is made up of 6-9%, by weight water, 20-30% by weight tetrahydrofuran, 2% or less by weight miscellaneous salts and high and low boilers and 61-74% by weight 1,4-butanediol. A slurry of crystals of 1,4-butanediol and liquid is formed. The solids content of the slurry is generally from 10-20% by weight. Slurry from the crystallizer is pumped into a centrifuge where crystals and mother liquor are separated. A wash solution made up of a mixture of tetrahydrofuran, refined 1,4-butanediol and water is introduced into the centrifuge to displace the mother liquor from the centrifuge cake.

To achieve other embodiments of the invention, a portion of the mother liquor and wash liquor is sent to a distillation column operated at atmospheric pressure where tetrahydrofuran and water are removed. Bottoms from said distillation which includes essentially all the impurities being added via the crude 1,4-butanediol are subjected to acid cyclization to convert to tetrahydrofuran any ingredients convertible to tetrahydrofuran. The other portion of the mother liquor is recycled to the crystallizer. The washed 1,4-butanediol crystals from the centrifuge are melted and then distilled to give three streams, one comprising tetrahydrofuran, 1,4-butanediol and water, one comprising refined 1,4-butanediol and the residue comprising high boilers. A portion of the tetrahydrofuran, 1,4-butanediol and water stream is used to wash the crystallized 1,4-butanediol. The remainder can be recycled to the crystallizer. Some of the refined 1,4-butanediol may be used to makeup additional wash liquid. The residue from the distillation of crystallized 1,4-butanediol is subject to acid cyclization to convert compounds to tetrahydrofuran that are convertible thereto. The tetrahydrofuran is recovered and/or further purified and the residue from cyclization disposed of.

In the examples that follow all references to parts and percentages are by weight unless otherwise indicated. The crude 1,4-butanediol used in the examples as a source of 1,4-butanediol, unless otherwise indicated, was obtained from a commercial process for the preparation of 1,4-butanediol from acetylene and formaldehyde and was typically of the following composition (after removal of inorganic salts):

|  | As Measured (%) | THF/H$_2$O Free Basis (%) |
|---|---|---|
| Water | 6.57 | 0 |
| Impurities which come off the gas chromotograph instrument before 1,4-butanediol | 0.593 | 0.635 |
| 1,4-butanediol | 92.482 | 98.985 |
| Impurities which come off the gas chromatograph instrument after 1,4-butanediol | 0.355 | 0.380 |

The impurities other than water varied about 0.2% depending on the process conditions. The water content varied from about 3% to about 10%.

A crystallizer equilibrium solution was prepared by adding crude 1,4-butanediol, 30% bottoms from crude 1,4-butanediol distillation, water and tetrahydrofuran to give the following formula:

| 1,4-butanediol | 76.8% by weight |
|---|---|
| THF | 14.2% by weight |
| H$_2$O | 5.0% by weight |
| Inorganic Salts/High Boilers | 4.0% by weight |

The 30% bottoms from crude 1,4-butanediol were prepared by distilling off 70% of the 1,4-butanediol in the crude 1,4-butanediol. The 30% bottom composition was by G.C. analysis:

| % impurities ahead of 1,4-butanediol | 0.422 |
|---|---|
| % 1,4-butanediol | 98.645 |
| % impurities after 1,4-butanediol | 0.932 |

EXAMPLE 1

A solution was prepared from 640 g of crude 1,4-butanediol, 210 g of 30% bottoms from crude 1,4-butanediol distillation, 142 g of refined tetrahydrofuran (THF) and 8 g of distilled water. A gas chromatographic analysis of the mixture was as follows:

| Analysis on a Water-Free Basis | |
|---|---|
|  | Analysis by G.C. |
| % THF | 14.89 |
| % coming off G.C. before 1,4-butanediol | 0.15 |
| % 1,4-butanediol | 84.54 |
| % coming off G.C. after 1,4-butanediol | 0.43 |
|  | 100.00 |

The solution was cooled to −8° C. in a roundbottom flask using moderate agitation, and an acetone-dry-ice bath. When crystallization began, the flask contents, which became a slurry of crystals, quickly warmed to −2° C. as the heat of crystallization was released. The slurry was cooled slowly to −4° C. and held there for about 30 minutes to complete the crystallization. The equilibrium slurry solids was about 19%.

The slurry was centrifuged using an International Equipment Company laboratory model centrifuge (Model CH) fitted with a Model 1341 stainless steel basket having a 100 mesh stainless steel screen. Loading of the slurry in the basket was done at about one-half speed to avoid carrying crystals over the lip of the basket. The crystals were washed using one volume of a mixture of THF and 1,4-butanediol having a freezing point of −4° C. (42% by weight tetrahydrofuran and 68% by weight 1,4-butanediol) per volume of mother liquor retained in the crystals.

The crystals were spun dry in the basket at top speed for 30 seconds before being removed for melting. The melted 1,4-butanediol was charged to a distillation flask and heated at atmospheric pressure to remove THF and water. The vacuum was lowered to 100 millimeters mercury pressure to complete the distillation. Four cuts were taken and analyzed by G.C. on a water-free basis as follows:

|  | Cut #1 | Cut #2 | Cut #3 | Cut #4 |
|---|---|---|---|---|
| % THF | 85.16 | 2.13 | 0.100 | 0.16 |
| % Components before BAD | 0.11 | 0.16 | 0.013 | 0.35 |
| % BAD | 14.73 | 97.71 | 99.987 | 99.44 |
| % Components after BAD | 0 | 0 | 0 | 0.05 |

No attempt was made in these tests to conduct the distillation so as to eliminate THF and water completely from the various cuts. The data show that a refined BAD product analyzing 99.987% on a THF/water-free basis can be produced from crude 1,4-butanediol which analyzes only 98.985% 1,4-butanediol on the same basis.

The 1,4-butanediol was tested for polyester color by measuring the APHA color in a Hach Chemical Company photometer of the reaction product of the 1,4-butanediol with adipic acid. 106 Grams of 1,4-butanediol were charged to a 3-neck, 500 ml roundbottom flask equipped with internal thermowell, nitrogen sparge tube and magnetic stirrer. 123 Grams of food processing-grade adipic acid were added to the flask. The flask was attached to a 12" Vigoreau column with water-cooled condenser connected to a vacuum source. The flask was evacuated three times to 10–20 millimeters mercury pressure and the vacuum broken each time using nitrogen gas to eliminate oxygen from the system. The agitator was started and the flask contents heated to 180° C. with a small bleed of nitrogen into the flask. The temperature was held at 180° C. for four hours. The nitrogen was then shut off. The flask was evacuated to 10 mm pressure, the temperature increased to 200° C. and held for two hours at 200° C. The flask contents were cooled to room temperature and the APHA color measured using a Hach Chemical Company photometer fitted with an alpha platinum-cobalt standard 5543 color filter. The result was 40 APHA. A sample of commercial grade distilled 1,4-butanediol was subjected to the same test and showed a 150 APHA.

The color absorbance for crystallized 1,4-butanediol was 0.002 as compared to 0.208 for commercial distilled 1,4-butanediol. The color absorbance for the 1,4-butanediol was obtained by placing 5 ml of 1,4-butanediol into a 25 ml Erlenmeyer flask. 5 ml of reagent-grade concentrated hydrochloric acid were added. The flask was stoppered and shaken to mix its contents. The stopper was removed and the contents of the 25 ml Erlenmeyer flask were transferred into a 1 cm×1 cm quartz cell and a stopper was inserted on the cell. The cell was placed in a spectrophotometer (Beckman Model 26 spectrophotometer) and allowed to stand about 30 minutes. At about 29.5 minutes, the spectrophotometer was switched to the absorbance mode, the chart/wavelength drive started and the absorbance maxima at 550, 500 and 450 nm recorded. The chart drive was stopped and the spectrophotometer was returned to the idle mode. The sample cell was removed, drained, rinsed and dried. The spectrophotometer was recalibrated at 500 and 650 nm using distilled water. The total absorbance was the sum of the 550, 500 and 450 absorbances.

EXAMPLE 2

The procedure of Example 1 was followed and the washed 1,4-butanediol analyzed by G.C. after distillation was 99.819% on a THF/water-free basis as compared to 98.985% for the crude 1,4-butanediol on the same basis.

EXAMPLE 3

The procedure of Example 1 was followed and the washed and distilled 1,4-butanediol analyzed by G.C. was 99.983% on a THF/water-free basis as compared to 98.985% for the crude 1,4-butanediol on the same basis. The washed and distilled BAD was subjected to the polyester color test described in Example 1. The result was 45 APHA.

EXAMPLE 4

The procedure of Example 1 was followed except that the 1,4-butanediol was not washed. The G.C. composition of the unwashed but distilled 1,4-butanediol was 99.951% on a THF/water-free basis as compared to 98.985% for the crude 1,4-butanediol on the same basis. The impurities removed after 1,4-butanediol on the G.C. were 0.049% as compared to 0.45% in the crude 1,4-butanediol.

EXAMPLE 5

Crude 1,4-butanediol, 30% bottoms from crude 1,4-butanediol, refined THF and water were used to prepare a solution equal in composition to that of Example 1. The solution was cooled in an agitated 5-gallon stainless jacketed crystallizer vessel to −3° C., to produce a 10% solids slurry, by direct contact with the vessel wall. A glycol-water coolant stream was circulated through the crystallizer jacket.

The 10% slurry was fed continuously to a Bird Company design solid bowl centrifuge (Model OBS 198) to separate the slurry crystals. The product exiting the crystal port of the centrifuge was a heavy slurry rather then dry crystals. Analysis of this product showed the level of impurities had been reduced from 0.833–0.544%.

EXAMPLE 6

A quantity of the slurry formed in Example 5 was taken from the 5-gallon stainless crystallizer of Example 5 and 1,4-butanediol crystals were centrifuged using an International Equipment Company Model CH laboratory centrifuge which had a Model 1341 stainless steel basket fitted with a 100 mesh stainless steel screen. A gas chromatographic analysis of unwashed crystals showed the 1,4-butanediol content to be 99.912% on a THF/water-free basis compared to 98.985% in the crude 1,4-butanediol. Distillation of the unwashed product gave a heart cut which analyzed 99.917% 1,4-butanediol on a THF/water-free basis.

EXAMPLE 7

The procedure of Example 6 was followed to obtain crystals of 1,4-butanediol. The crystals were washed on the centrifuge basket using a quantity of 50% THF-50% 1,4-butanediol mixture equal to a one-volume displacement of the liquor retained on the centrifuged crystals. The washed crystals analyzed 99.957% 1,4-butanediol on a THF/water-free basis compared to 98.985% 1,4-butanediol for the crude 1,4-butanediol on the same basis.

EXAMPLE 8

The procedure of Example 6 was followed to obtain crystals of 1,4-butanediol. The crystals were washed as in Example 7 except the wash was equal to two-volume displacements of liquor. Distillation of the melted crystals gave a heart cut which analyzed 99.964% 1,4-butanediol on a THF/water-free basis as compared to 98.985% for the crude 1,4-butanediol.

Total color absorbance of the heart cut material was 0.008 compared to 0.208 for 1,4-butanediol that had been merely double distilled.

EXAMPLE 9

The procedure of Example 6 was followed to obtain crystals of 1,4-butanediol. The crystals were washed as in Example 7 except the wash was equal to three-volume displacement of liquor. Analysis of the washed crystals showed 99.981% 1,4-butanediol compared to 98.985% for the crude 1,4-butanediol on a THF/water-free basis.

The following comparison of 1,4-butanediol quality further illustrates the advantages of the present invention:

| Percent of Impurities from Gas Chromatograph Analysis* | | |
|---|---|---|
| Before 1,4-Butanediol | 1,4-Butanediol | After 1,4-Butanediol |
| Crude 1,4-butanediol Distilled Only | | |
| 0.635 | 98.985 | 0.380 |
| Crude 1,4-butanediol | | |
| 0.225 | 99.399 | 0.376 |
| Crude 1,4-butanediol | 0.203 | 99.553 | 0.244 |
| Crude 1,4-butanediol | 0.144 | 99.487 | 0.369 |
| Crude 1,4-butanediol | 0.342 | 99.372 | 0.286 |
| Crude 1,4-butanediol Crystallized by present | 0.073 | 98.913 | 0.987 |

| Percent of Impurities from Gas Chromatograph Analysis* | | | |
|---|---|---|---|
| | Before 1,4-Butanediol | 1,4-Butanediol | After 1,4-Butanediol |
| process | | | |
| Unwashed-undistilled | 0.041 | 99.910 | 0.049 |
| Washed-distilled | 0.013 | 99.987 | 0 |

*THF/water-free basis

While certain representative embodiments and details have been shown for the purpose of illustration the invention, it will be apparent to those skilled in the art that various changes and modifications may be made therein without departing from the spirit and scope of the invention.

INDUSTRAIL APPLICABILITY

The present process enables one to purify crude 1,4-butanediol to a higher purity than heretofore possible by distillation. Thus, it permits the production of higher purity 1,4-butanediol and it permits the production of 1,4-butanediol without an additional impurity. In the process of the present invention it is convenient to commercially produce 1,4-butanediol and to also produce tetrahydrofuran from the liquid used in the crystallization. The process of the invention is useful in the preparation of high purity 1,4-butanediol while recovering all 1,4-butanediol that is "lost" in the crystallization liquid by converting it to tetrahydrofuran.

I claim:

1. A process for purifying 1,4-butanediol, the process comprising
   (a) crystallizing 1,4-butanediol from a crude liquid comprising
      (1) 35-85%, by weight, of 1,4-butanediol and
      (2) 2-15%, by weight, of impurities dissolved in tetrahydrofuran, by holding the liquid at a temperature of −10° C. to +10° C., to form a slurry of 1,4-butanediol crystals; and then
   (b) separating the crystals from the crude liquid.

2. The process of claim 1 wherein the separation is achieved with a centrifuge.

3. The process of claim 2 wherein the centrifuge has a perforated bowl.

4. The process of claim 1 wherein the crystals in the slurry of step (a) constitute 10-20% of its weight.

5. The process of claim 1 wherein the temperature in step (a) is held at −4° C. to +4° C. and the pressure is held at 16-26 mm of mercury absolute.

6. The process of claim 1 wherein the crystals separated in step (b) are washed with a wash solution comprising
   (a) tetrahydrofuran,
   (b) water, and
   (c) optionally, 1,4-butanediol,
and are then separated from the wash solution.

7. A process for purifying 1,4-butanediol, the process comprising
   (a) crystallizing 1,4-butanediol from a crude liquid comprising
      (1) 35-85%, by weight, of 1,4-butanediol and
      (2) 2-15%, by weight, of impurities dissolved in
      (3) 14-50%, by weight, of tetrahydrofuran, by holding the liquid at a temperature of −4° C. to +4° C. and under a pressure of 16-26 mm of mercury absolute, to form a slurry of crystals in which the crystals constitute 10-20% of its weight;
   (b) separating the crystals from the crude liquid;
   (c) washing the crystals with a wash solution comprising
      (1) tetrahydrofuran,
      (2) water, and
      (3) optionally, 1,4-butanediol, and then
   (d) separating the crystals from the wash solution.

8. The process of claim 1, 2, 3, 4, 5, 6 or 7 in which the butanediol to be purified is made by catalytically reacting acetylene and formaldehyde to form 1,4-butynediol and then hydrogenating the butynediol to form 1,4-butanediol.

9. The process of claim 1, 2, 3, 4, 5, 6 or 7 in which the butanediol to be purified is obtained from the reaction of propylene and acrolein.

10. The process of claim 1, 2, 3, 4, 5, 6 or 7 in which the butanediol to be purified is obtained from furan.

11. The process of claim 1 having the additional step of catalytically converting the residual 1,4-butanediol in at least a portion of the crude liquid from step (b) to tetrahydrofuran and recycling the said tetrahydrofuran to the crude liquid in step (a).

12. The process of claim 6, 7 or 11 having the additional step of catalytically converting the residual 1,4-butanediol in the used wash liquid to tetrahydrofuran and recycling the said tetrahydrofuran to the crude liquid in step (a).

13. The process of claim 1 in which the temperature in (a) (2) is held at −10° C. to +10° C. by evaporative cooling.

* * * * *